(12) United States Patent
Roberts

(10) Patent No.: US 6,715,722 B2
(45) Date of Patent: Apr. 6, 2004

(54) SUPPORT STRUCTURE FOR MOUNTING EQUIPMENT TO TRANSPORTABLE ANESTHESIA MACHINES

(76) Inventor: William Alan Roberts, 1130 Bauy Rd., Fairfield, VT (US) 05455

( * ) Notice: Subject to any disclaimer, the term of this patent is extended or adjusted under 35 U.S.C. 154(b) by 147 days.

(21) Appl. No.: 09/970,854

(22) Filed: Oct. 5, 2001

(65) Prior Publication Data

US 2002/0040954 A1 Apr. 11, 2002

Related U.S. Application Data

(60) Provisional application No. 60/237,674, filed on Oct. 5, 2000.

(51) Int. Cl.[7] ............................................. A45D 19/04
(52) U.S. Cl. ...................... 248/129; 248/127; 248/133; 248/317; 248/214
(58) Field of Search ................. 248/129, 127, 248/133, 371, 415, 121, 229.1, 227.4, 229.2, 214, 229.15, 231.85, 317, 231.61, 177.1, 125.7, 616, 122.1; 108/49

(56) References Cited

U.S. PATENT DOCUMENTS

| | | | | | |
|---|---|---|---|---|---|
| 1,797,847 A | * | 3/1931 | Vandagriff | .................. | 108/49 |
| 1,862,237 A | * | 6/1932 | Pepler | .......................... | 108/49 |
| 1,957,165 A | * | 5/1934 | Gingras | ........................ | 108/49 |
| 2,460,244 A | * | 1/1949 | Strauss | ........................ | 108/137 |
| 2,535,112 A | * | 12/1950 | Woody | ........................ | 312/233 |
| 2,605,155 A | * | 7/1952 | Lewis | ......................... | 108/139 |
| 2,703,265 A | * | 3/1955 | Wolfe | .......................... | 248/214 |
| 5,144,898 A | * | 9/1992 | Posly | ........................... | 108/148 |
| 5,893,607 A | * | 4/1999 | Trimnell | ..................... | 297/170 |
| 6,213,435 B1 | * | 4/2001 | Minet | ....................... | 248/125.8 |
| 6,231,016 B1 | * | 5/2001 | Slone | ........................ | 248/200.1 |

* cited by examiner

Primary Examiner—Kimberly Wood

(57) ABSTRACT

A support structure for mounting equipment, such as a video monitor, to a transportable anesthesia machine includes an elongate vertical member adapted to mount the video monitor and/or other equipment and an elongate horizontal member extending perpendicularly from the vertical member for removable attachment to the anesthesia machine. The horizontal member extends from a lower end of the vertical member and is removably attached to a frame of the anesthesia machine in a desired angular position. The support structure and anesthesia machine move as a unit when the anesthesia machine is transported along a floor surface, with the video monitor or other equipment disposed at an advantageous location for use by an anesthesiologist during a medical procedure. The support structure has a foot that prevents or inhibits undesired tipping or tilting of the anesthesia machine.

20 Claims, 2 Drawing Sheets

SUPPORT STRUCTURE FOR MOUNTING EQUIPMENT TO TRANSPORTABLE ANESTHESIA MACHINES

CROSS-REFERENCE TO RELATED PATENT APPLICATIONS

This application claims the benefit of priority from U.S. Provisional patent application Ser. No. 60/237,674 filed Oct. 5, 2000, the disclosure of which is incorporated herein by reference.

BACKGROUND OF THE INVENTION

1. Field of the Invention

The present invention relates to transportable anesthesia machines and, more particularly, to support structure attachable to transportable anesthesia machines for mounting equipment, such as a video monitor, to the transportable anesthesia machines.

2. Brief Description of the Related Art

Transportable anesthesia machines are currently used in operating rooms and similar sites to deliver anesthesia to patients undergoing medical procedures. Examples of anesthesia machines include the Narkomed 1A, 2A and 2B anesthesia machines of North American Drager. Such machines typically include an anesthesia delivery system carried on and/or in a cart having a wheeled frame. The frame includes a pair of parallel side members and a pair of cross members extending between the side members. The frame is normally exposed and externally accessible beneath the cart. The frame is attached to wheels, allowing the cart to be transported or maneuvered along a floor surface.

Patient monitoring systems are used with transportable anesthesia machines and typically include a video monitor, such as the Hewlett-Packard video monitor typically used with the Narkomed anesthesia machines of North American Drager. The patient monitoring systems typically detect or measure various parameters, such as heart rate, blood pressure, pulse and gas concentrations, and provide a visual display on the display screen of the video monitor. The display screen of the video monitor is observed by the anesthesiologist to assess the patient's medical condition throughout the medical procedure being performed.

Conventional transportable anesthesia machines support the video monitors on top of the anesthesia machines. When thusly supported, the video monitors are positioned higher than desirable so that the head of a seated anesthesiologist must be rotated to the right and tilted upward in order to visualize the display screens. This is uncomfortable for the anesthesiologist, may contribute to physician fatigue and interferes with continuous observation of the patient. In addition, mounting of the video monitors on top of the anesthesia machines raises the center of gravity of the anesthesia machines, possibly increasing the risk of the anesthesia machines tilting or tipping over. Present arrangements for supporting video monitors on anesthesia machines give rise to additional drawbacks including equipment and instrumentation not being within easy visualization and reach of the anesthesiologist, susceptibility for tangling of cords and hoses, the risk of injury and damage due to falling equipment, and difficulties in transportation and cleaning.

SUMMARY OF THE INVENTION

Accordingly, it is a primary object of the present invention to overcome the aforementioned disadvantages of supporting equipment relative to transportable anesthesia machines.

Another object of the present invention is to mount a video monitor or other equipment to a transportable anesthesia machine without raising the center of gravity of the anesthesia machine.

A further object of the present invention is to mount a video monitor and its control panel or other equipment to a transportable anesthesia machine so that the video monitor, gauges, flow meter and patient are within a single visual field for an anesthesiologist.

An additional object of the present invention is to mount a video monitor or other equipment to a transportable anesthesia machine so that the display screen of the video monitor is at eye level for a seated anesthesiologist and positioned between the patient and the anesthesia machine controls.

It is also an object of the present invention to mount a video monitor or other equipment to a transportable anesthesia machine in a manner imparting improved tilt resistance to the anesthesia machine.

Some of the advantages of the present invention are that all equipment and instrumentation are visible by and within easy reach of the anesthesiologist, the video monitor is able to swivel and tilt, the location of the video monitor outwardly from the anesthesia machine is adjustable, easy access to the bellows is afforded, the risk of tangling of cords and hoses is reduced, the support structure and equipment mounted thereto move as one unit with the anesthesia machine thereby facilitating transport, the support structure is without textured surfaces and is thusly conducive to cleaning, the risk of injury or damage due to falling equipment is reduced, the support structure can be packaged and shipped in a disassembled condition, the support structure is easily assembled with the use of standard tools, the support structure is readily attachable to conventional transportable anesthesia machines as well as being readily detachable therefrom, the support structure can be provided of non-ferrous materials for use in environments with magnetic resonance imaging, the bolt and bolt holes originally supplied with conventional video monitors are used to mount the video monitors on the support structure, the support structure can be used to mount various diverse equipment used with anesthesia machines, and the support structure can be easily adapted for use with various diverse conventional transportable anesthesia machines.

These and other objects, advantages and benefits are realized with the present invention as generally characterized in a support structure for mounting equipment, such as a video monitor, to a transportable anesthesia machine having a wheeled frame including a pair of exposed, parallel side members. The support structure includes an elongate vertical member and an elongate horizontal member extending perpendicularly from the vertical member for removable attachment to the frame of the anesthesia machine. The vertical member has an upper end at which the equipment is mounted and has a lower end. The horizontal member has an inboard end attached to the lower end of the vertical member and has a free outboard end. Preferably, the horizontal member is removably attached to the vertical member. A preferred removable attachment for the horizontal member to the vertical member includes a perpendicular flange on the lower end of the vertical member bolted to the inboard end of the horizontal member. The horizontal member is secured, preferably removably, to the frame of the anesthesia machine so that the support structure and the anesthesia machine move as a unit when the anesthesia machine is transported or wheeled along a floor surface. The horizontal member crosses the side members of the frame transversely, and the support structure includes one or more retaining plates connected to the horizontal member in adjustable spaced relation therewith so that the side members are compressively retained between the horizontal member and the one or more retaining plates. Preferably, two retaining plates are provided in the support structure, one for each side member. Each retaining plate has opposing ends extending laterally beyond opposing sides of the corresponding side member. Bolts extend through the opposing ends of the retaining plates to be disposed on opposite sides of the side members, respectively. The bolts extend through the horizontal member and have ends that protrude from the horizontal member. Nuts are secured on the ends of the bolts, respectively, to connect the retaining plates and the horizontal member in adjustable spaced relation. The nuts are tightened on the bolts to compressively secure the side members of the anesthesia machine between the retaining plates and the horizontal member. The retaining plates and bolts allow the horizontal member to be angularly adjusted relative to the side members of the anesthesia machine. The support structure includes a foot that depends from the horizontal member to a lower end disposed close to the floor surface. The foot inhibits or prevents undesired tilting or tipping over of the anesthesia machine. The vertical member support the video monitor and/or other equipment outwardly from the anesthesia machine. The video monitor and/or other equipment mounted at the upper end of the vertical member is advantageously disposed below a top of the anesthesia machine at a desirable location for viewing by an anaesthesiologist during a medical procedure.

Other objects and advantages of the present invention will become apparent from the following description of the preferred embodiments taken in conjunction with the accompanying drawings, wherein like parts in each of the several figures are identified by the same reference numerals.

DESCRIPTION OF THE PREFERRED EMBODIMENT

Figure 1:
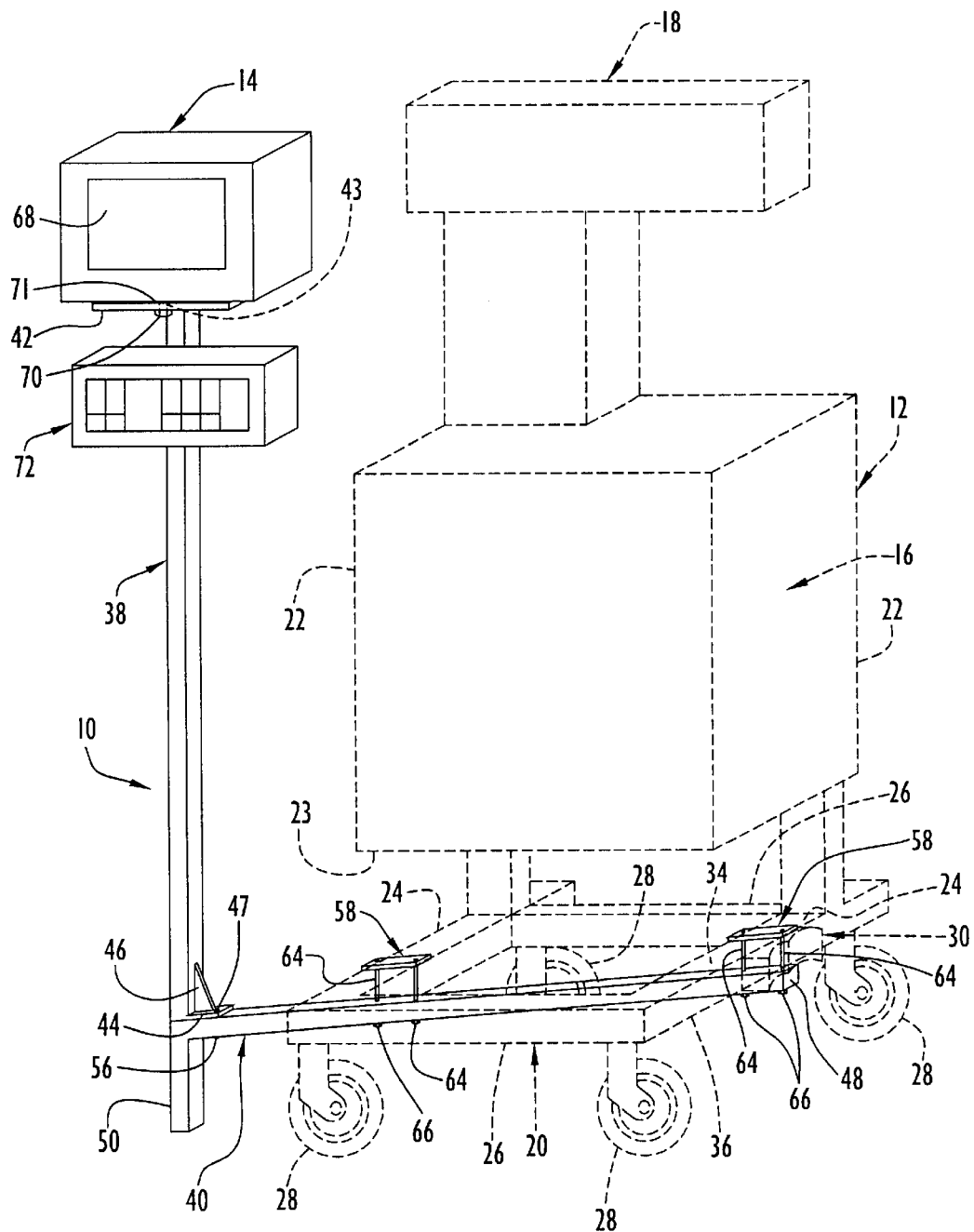
FIG. 1 is a perspective view illustrating the support structure of the present invention attached to a transportable anesthesia machine and mounting a video monitor to the transportable anesthesia machine.

A support structure 10 according to the present invention is illustrated in FIG. 1 attached to a transportable anesthesia machine 12 and mounting a video monitor 14 relative to the anesthesia machine 12. The anesthesia machine 12 is a conventional, transportable anesthesia machine such as the Narkomed 1A, 2A or 2B anesthesia machines of North American Drager. The anesthesia machine 12, which is shown in dotted lines, includes a cart 16, an anesthesia delivery system 18 carried on and/or in the cart 16 for delivering anesthesia to a patient undergoing a medical procedure, and a frame or base 20 attached to cart 16. The frame 20 is located on the underside of cart 16, the frame 20 being spaced beneath sides 22 and bottom 23 of the cart 16. Accordingly, the frame 20 is not enclosed, but is externally exposed and accessible beneath cart 16.

Figure 2:
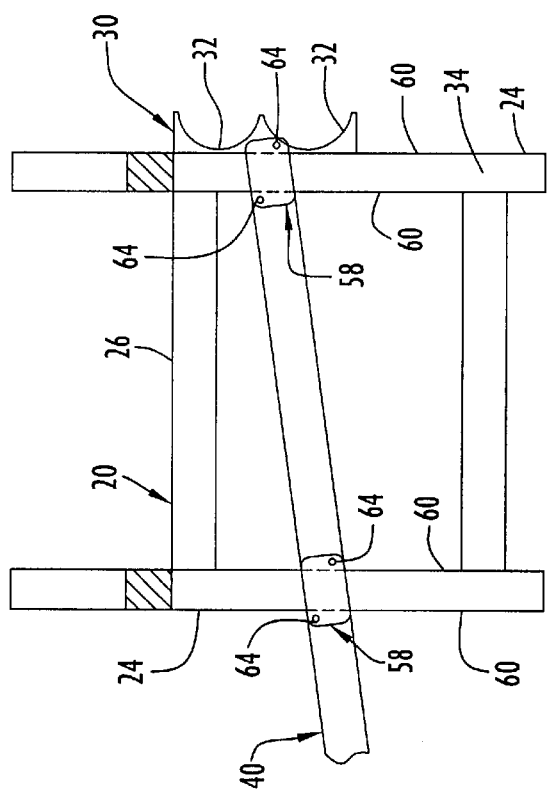
FIG. 2 is a broken, top plan view illustrating the support structure attached to the frame of the anesthesia machine.

The frame 20 includes a pair of parallel side members 24 and a pair of parallel cross members 26 extending between the side members 24 as shown in FIGS. 1 and 2. The frame 20 is attached to four wheels 28 located at the four corners, respectively, of the square configuration defined by the side and cross members. The wheels 28 allow the anesthesia machine 12 to be transported or otherwise maneuvered by rolling on or along a floor surface.

A yoke 30 may be provided on frame 20 as shown in FIGS. 1 and 2 for the right side member 24. The yoke 30 defines concave recesses 32 for receiving cylindrical tanks, such as oxygen tanks (not shown), mounted to the anesthesia machine 12. The yoke 30 typically extends in the vertical direction between planar upper and lower surfaces 34 and 36, respectively, of the right side member as shown in FIG. 1. Two recesses 32 arranged side by side are shown for the illustrative anesthesia machine.

The support structure 10 includes an elongate vertical member 38 and an elongate horizontal member 40 extending perpendicularly to vertical member 38. The vertical member 38 has an upper free end, and a planar, horizontal support plate 42 extending forwardly from the upper end of the vertical member. A hole 43 is pre-drilled in the support plate 42 for receiving a bolt used to fasten the video monitor 14 on the support plate as explained further below. A planar flange 44 extends perpendicularly from a lower end of the vertical member. A gusset 46 is disposed in the inside corner defined by vertical member 38 and flange 44, and is welded thereto. The gusset 46 provides increased strength to the support structure 10. Holes are pre-drilled in flange 44, preferably two on each side of gusset 46, for receiving bolts 47, respectively, used to secure vertical member 38 to horizontal member 40 as explained further below. Only one bolt 47 is visible in FIG. 1.

The horizontal member 40 has a free outboard end 48 and an inboard end provided with a depending vertical foot 50. The foot 50 extends perpendicular to the horizontal member 40 and terminates at a lower end. The foot 50 is in axial alignment with the vertical member 38 when the vertical member is bolted to the horizontal member as explained further below. Holes are pre-drilled in the horizontal member 40 in alignment with the holes of flange 44, respectively, when the foot 50 is axially aligned with the vertical member 38. Although the foot 50 is preferably formed as part of the horizontal member, it should be appreciated that the foot can be formed as a lower extension of vertical member 38.

Figure 3:
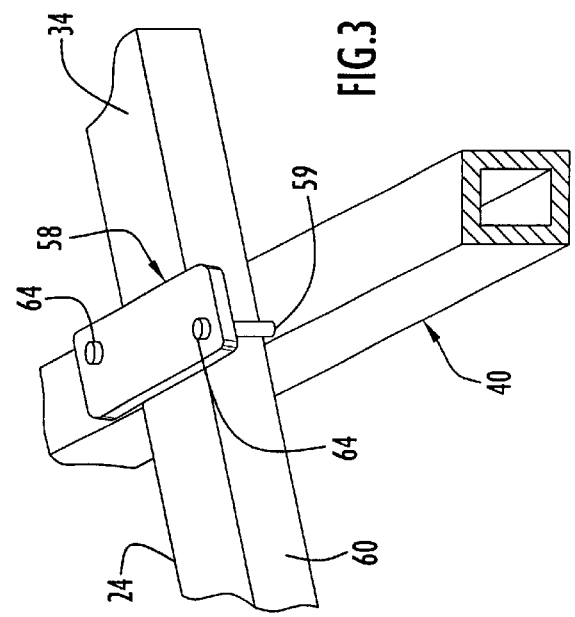
FIG. 3 is a fragmentary perspective view illustrating a side member of the frame retained between a retaining plate and the horizontal member of the support structure.

The support structure 10 is attached to the anesthesia machine 12 and, in particular, the horizontal member 40 is attached to the frame 20. As best shown in FIGS. 2 and 3, the horizontal member 40 is positioned to cross side members 24 and extend in a direction transverse thereto. The horizontal member 40 is secured to side members 24 via one or more planar retaining or securing plates secured to the horizontal member by bolts. One retaining plate 58 is provided for each side member 24 in a preferred embodiment, with each side member being sandwiched between a retaining surface of retaining plate 58 and an abutment surface of horizontal member 40. The horizontal member 40 extends at an angle to the side members 24 with the abutment surface, as defined by a planar upper surface of the horizontal member 40, in engagement or abutment with the planar lower surfaces 36 of the side members 24, respectively. It should be appreciated that the horizontal member 40 can cross over, rather than under, the side members 24 with the abutment surface defined by a planar lower or bottom surface of the horizontal member disposed on or in abutment with the planar top surfaces 34 of the side members, respectively, in a simple rearrangement of parts. The arrangement illustrated herein is preferred, however, for greater stability.

Each retaining plate 58 straddles or extends across the width of a corresponding side member 24, with the retaining surface of the retaining plate 58 in engagement with the planar upper surface 34 of the corresponding side member as best shown in FIGS. 2 and 3. Opposing ends of each retaining plate 58 extend beyond the width of the corresponding side member 24; and, accordingly, the opposing ends are disposed laterally outwardly of opposing sides 60 of the corresponding side member 24. Each retaining plate 58 has holes pre-drilled in the opposing ends thereof, with the holes of the retaining plates disposed outwardly of the opposing sides 60 of the corresponding side member. Holes 59, one of which is shown in FIG. 3, are pre-drilled through the horizontal member 40 and are vertically aligned with the holes of the retaining plates, respectively.

As a guide to facilitate installation of the support structure 10 on the anesthesia machine 12, the outboard end 48 of horizontal member 40 is disposed at the juncture of recesses 32 but does not obstruct the recesses 32. The holes of the retaining plates may or may not be centered on the ends of the retaining plates. In FIGS. 2 and 3, the holes of each retaining plate 58 are shown longitudinally offset from one another to enhance adjustability of the horizontal member 40. Preferably, the retaining plates 58 have a width about the same as the width of the horizontal member 40 and a length extending in the same direction as the length of the horizontal member 40. The corners of the retaining plates are preferably rounded for enhanced safety.

The side members 24 are compressively sandwiched between the horizontal member 40 and the retaining plates 58 using compression bolts 64 inserted through the holes of the retaining plates and the holes 59 of the horizontal member aligned therewith. As shown in FIG. 3 for the left side member 24, the holes of the retaining plate 58 are aligned with the holes 59 of the horizontal member 40 so that a pair of aligned holes is disposed on each side of the left side member 24. The compression bolts 64 are inserted through the aligned holes so that ends of the compression bolts 64 protrude from the lower surface of the horizontal member 40. Nuts 66, shown in FIG. 1, are threaded onto the protruding ends of compression bolts 64 to connect the retaining plates to the horizontal member in adjustable, spaced relation therewith. The nuts 66 are tightened to move the retaining plates 58 toward the horizontal member 40 to compressively secure the side members 24 between the abutment surface of horizontal member 40 and the retaining surfaces of retaining plates 58. The compression bolts 64 span the vertical space between the retaining plates 58 and the horizontal member 40, thereby confining each side member 24 laterally between a pair of compression bolts. It should be appreciated that the horizontal member 40 can be secured to frame 20 in various ways other than the retaining plates 58 and bolts 64 shown herein.

The vertical member 38 is thereafter assembled to the horizontal member 40 by aligning the holes of flange 44 with the corresponding holes of horizontal member 40, and inserting bolts 47 through the aligned holes, respectively. The ends of bolts 47 are inserted through the holes of flange 44 and are passed through the holes of horizontal member 40 aligned therewith so that the ends of the bolts 47 protrude from the planar lower surface of horizontal member 40. Nuts 56 are threaded onto the protruding ends of bolts 47, only one of which is visible in FIG. 1. Nuts 56 are tightened to secure the vertical and horizontal members together, with flange 44 supported on the planar upper surface of horizontal member 40. The support structure 10 can be disassembled merely by untightening nuts 56 from bolts 47, and removing bolts 54 from the aligned holes. Of course, the vertical member 38 can be secured, preferably removably, to the horizontal member 40 in many various ways other than the flange 44 and bolts 47 shown herein.

In FIG. 2, the support structure is shown attached to the anesthesia machine with the horizontal member 40 non-perpendicular to side members 24. It should be appreciated, however, that the compression bolts 64 can be loosened via untightening of nuts 66 to allow pivotal movement of horizontal member 40 relative to side members 24. In this manner, the angle or orientation of the horizontal member 40 with the side members 24 can be adjusted, and the horizontal member 40 can be secured in various adjusted angular positions, including a perpendicular position, via tightening of nuts 66. The retaining flanges 58 and bolts 64 disclosed herein are thusly representative of an adjustable securing means for adjustably securing the support structure to the anesthesia machine. However, various non-adjustable securing means could be utilized.

The video monitor 14, as shown in FIG. 1, is a conventional video monitor of the type typically used in conjunction with anesthesia monitoring systems. As an example, the video monitor 14 can be a Hewlett-Packard video monitor of the type conventionally used with the Narkomed anesthesia machines of North American Drager. The video monitor 14 forms part of a patient monitoring system conventionally used to detect and measure various parameters, such as heart rate, blood pressure, pulse and gas concentrations. The video monitor includes a display screen 68 upon which various parameters are displayed for visualization by an anesthesiologist. The video monitor 14 is typically supplied by the manufacturer with a bolt 70 for insertion in a pre-formed hole (not shown) in the video monitor.

In accordance with the present invention, the video monitor 14 is removably secured upon the support plate 42 of support structure 10 using the bolt 70 and the pre-formed hole in the video monitor. As shown in FIG. 1, the video monitor 14 is placed upon the support plate 42, and the end of bolt 70 is inserted through the pre-drilled hole 43 in support plate 42. Bolt 70 is threaded into the pre-formed hole in the video monitor 14, which is supplied with a rubber gasket 71 allowing the video monitor to swivel and/or tilt relative to the vertical member 38 after being secured to the support plate 42. The monitor tilt mechanics are retained and functional with this application. When the video monitor 14 is secured on the vertical member 38, the screen 68 is disposed below the top of the anesthesia machine 12, and is not disposed above the top of the anesthesia machine as it would be if the monitor was conventionally mounted on the top of the anesthesia machine. It should be appreciated that the support plate 42 can be mounted on the vertical member 38 in a manner allowing the support plate itself to tilt and/or swivel, and a universal ball joint mounting can thusly be used by way of example to mount the support plate to the vertical member.

In a preferred embodiment, the vertical member 38 of the support structure 10 is made from one and one half inch square steel tubing. The overall height of the support structure 10 from the lower end or bottom of foot 50 to the upper end of vertical member 38 is about four feet, two and one eighth inches, approximately the center of the interpupilary plane of the seated anesthetist. The overall width of the support structure 10 from the outboard end 48 to the outer side of foot 50 is about three feet, one and one quarter inches. The vertical member 38 is typically disposed about one foot laterally outwardly of the anesthesia machine to which the support structure is attached. Foot 50 protrudes about four inches below the lower or bottom surface of horizontal member 40. Retaining plates 58 each have a width of about two inches, a length of about five inches and a depth or thickness of about one quarter inch. The horizontal member 40 and foot 50 are made with two and one quarter inch square steel tubing.

When mounted to the anesthesia machine 12 by support structure 10, the video monitor 14 is disposed alongside the anesthesia machine in a desirable position. The position of the vertical member 38 and, therefore, the video monitor 14, outwardly from the anesthesia machine 12 can be adjusted via rotational or pivotable movement of horizontal member 40, allowing the video monitor to be optimally positioned for particular circumstances. The video monitor 14, the control panel, gauges, flow meter and the patient are within a single visual field for an anesthesiologist seated in front of the video monitor. The control modules 72 for the monitoring system can be easily mounted on the vertical member 38 using their standard pole mount clamp as shown in FIG. 1. All instrumentation is maintained within easy reach of the anesthesiologist and is highly visible. The bellows is easily accessible. The ability for the video monitor to swivel and tilt is maintained. The risk of tangling cords and hoses is reduced. By mounting the video monitor alongside the anesthesia machine rather than on top of the anesthesia machine, the center of gravity of the anesthesia machine is not increased. Rather, the low center of gravity resulting from use of support structure 10 inhibits tipping of the anesthesia machine and may actually improve tilt-test results. The lower end of foot 50 is disposed close to but does not contact the floor surface, thusly permitting the floor beneath the foot to be mopped. However, the foot adds stability to the anesthesia machine and prevents or inhibits tipping or tilting. An anesthesiologist seated before the video monitor is able to see the monitor, the patient, and instrumentation without requiring the head of the anesthesiologist to be tilted upwardly or rotated. Accordingly, physician discomfort and fatigue are reduced, and continuous observation of the patient and monitors is enhanced. The video monitor is optimally positioned so that the eyes of a seated anesthesiologist are centered on the display screen without tilting of the head. The support structure and the equipment attached to it are secured to the frame or base of the anesthesia machine so there is less risk of injury or damage due to falling equipment. The support structure 10 is adapted for packaging and shipping in an unassembled condition. The support structure 10 is easily assembled and is easily attached to the anesthesia machine with standard tools. The support structure 10 is preferably fabricated from rigid square tubing having an epoxy finish. The support structure 10 may be fabricated of non-ferrous materials for use in environments having magnetic resonance imaging. The support structure can be retrofit to various conventional anesthesia machines. The support structure 10 can be used to support or mount various equipment relative to the anesthesia machines.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A support structure for mounting equipment to a transportable anesthesia machine having a wheeled frame, said support structure comprising an elongate vertical member adapted to mount the equipment which is to be mounted to the anesthesia machine, said vertical member having an upper end and a lower end;

an elongate horizontal member extending perpendicularly from said lower end of said vertical member, said horizontal member having an inboard end attached to said vertical member and having an outboard end;

means for securing said horizontal member to the frame of the anesthesia machine so that said vertical member is disposed alongside the anesthesia machine and said support structure moves as a unit with the anesthesia machine when the anesthesia machine is transported, said means for securing including a retaining plate adjustably connected to said horizontal member for movement toward said horizontal member to compressively secure the frame between said retaining plate and said horizontal member; and a vertical foot extending downwardly from said horizontal member in a perpendicular direction, said foot being axially aligned with said vertical member.

2. A support structure as recited in claim 1 wherein said inboard end of said horizontal member is removably attached to said vertical member.

3. A support structure for mounting equipment to a transportable anesthesia machine having a wheeled frame, said support structure comprising:

an elongate vertical member adapted to mount the equipment which is to be mounted to the anesthesia machine, said vertical member having an upper end and a lower end;

an elongate horizontal member extending perpendicularly from said lower end of said vertical member, said horizontal member having an inboard end attached to said vertical member and having an outboard end;

means for securing said horizontal member to the frame of the anesthesia machine so that said vertical member is disposed alongside the anesthesia machine and said support structure moves as a unit with the anesthesia machine when the anesthesia machine is transported:

a vertical foot extending downwardly from said horizontal member in a perpendicular direction, said foot being axially aligned with said vertical member; and a flange extending perpendicularly from said lower end of said vertical member and at least one bolt for removably bolting said flange to said horizontal member.

4. A support structure as recited in claim 3 and further including a gusset secured between said vertical member and said flange.

5. A support structure as recited in claim 1 wherein said means for securing further includes one or more bolts adjustably connecting said retaining plate to said horizontal member.

6. A support structure as recited in claim 1 wherein said foot is formed integrally, unitarily with said horizontal member.

7. A support structure for mounting a video monitor to an anesthesia machine having a wheeled frame transportable on a floor surface and including a pair of parallel side members, said support structure comprising an elongate vertical member having an upper end for removably mounting the video monitor thereon and having a lower end;

an elongate horizontal member extending perpendicularly from said lower end of said vertical member, said horizontal member having an inboard end attached to said vertical member, an outboard end and an abutment surface between said inboard end and said outboard end for abutment with at least one of the side members of the frame;

means for adjustably, removably securing said horizontal member to the at least one side member of the frame with said horizontal member extending transversely to the at least one side member to position the video monitor alongside the anesthesia machine, said means for adjustably, removably securing including at least one retaining surface adjustably connected in spaced relation with said abutment surface to compressively secure the at least one side member between said retaining surface and said abutment surface; and means for preventing tipping of the anesthesia machine.

8. A support structure as recited in claim 7 wherein said elongate vertical member and said elongate horizontal member are made from square tubing.

9. A support structure as recited in claim 8 wherein said tubing is made of steel.

10. A support structure as recited in claim 7 and further including means on said upper end of said vertical member for mounting the video monitor in a manner allowing the video monitor to swivel relative to said vertical member.

11. A support structure as recited in claim 10 wherein said means for mounting includes a planar support plate at said upper end of said vertical member and a bolt for securing the video monitor to said support plate.

12. A support structure for mounting a video monitor to an anesthesia machine having a wheeled frame transportable on a floor surface and including a pair of parallel side members, said support structure comprising an elongate vertical member having an upper end for removably mounting the video monitor thereon and having a lower end;

an elongate horizontal member extending perpendicularly from said lower end of said vertical member, said horizontal member having an inboard end attached to said vertical member and having a free outboard end;

means for adjustably, removably securing said horizontal member to the side members of the frame with said horizontal member extending transversely to said side members to position the video monitor alongside the anesthesia machine at a location below a top of the anesthesia machine, said means for adjustably, removably securing including a pair of retaining plates connected to said horizontal member in adjustable spaced relation therewith, the side members of the frame being compressively secured between said retaining plates, respectively, and said horizontal member; and means for preventing tipping of the anesthesia machine.

13. A support structure as recited in claim 12 wherein said means for preventing includes a foot depending from said horizontal member in a perpendicular direction and terminating at a lower end disposed close to but above the floor surface.

14. A support structure for mounting a video monitor to a transportable anesthesia machine having a wheeled frame including a pair of parallel side members, said support structure comprising an elongate vertical member having an upper end for removably mounting the video monitor thereon and having a lower end;

an elongate horizontal member having an inboard end removably attached to said lower end of said vertical member and having a free outboard end, said horizontal member extending perpendicularly to said vertical member with said horizontal member crossing the side members of the frame;

a retaining plate disposed over each of the side members of the frame so that each side member is positioned between one of said retaining plates and said horizontal member;

a plurality of bolts for securing said retaining plates to said horizontal member to compressively secure the side members of the frame between said retaining plates and said horizontal member, said bolts being disposed on opposite sides of each of the side members to constrain the side members laterally; and a foot depending from said lower end of said vertical member to inhibit tilting of the anesthesia machine.

15. A support structure as recited in claim 14 and further including a planar horizontal support plate extending forwardly from said upper end of said vertical member and a bolt extending through said support plate for securing the video monitor thereon.

16. A support structure as recited in claim 14 wherein said horizontal member is disposed beneath the side members of the frame and said retaining plates are disposed over the side members of the frame.

17. A support structure as recited in claim 16 wherein each of said retaining plates has opposing ends disposed laterally outwardly of the opposite sides of the side members, respectively.

18. A support structure as recited in claim 17 wherein said plurality of bolts includes a pair of bolts for each of said retaining plates, one of said pair of bolts including first and second bolts disposed through said opposing ends, respectively, of one of said retaining plates, the other of said pair of bolts including first and second bolts disposed through said opposing ends, respectively, of the other of said retaining plates.

19. A support structure as recited in claim 18 wherein said bolts extend through holes, respectively, in said horizontal member and have ends protruding from a lower surface of said horizontal member.

20. A support structure as recited in claim 19 and further including nuts secured on said ends of said bolts, respectively, and capable of tightening to compressively secure the side members between said retaining plates and said horizontal member.

* * * * *